United States Patent [19]

Trist et al.

[11] 4,117,597
[45] Oct. 3, 1978

[54] DENTAL DRILL

[75] Inventors: Nicolas P. Trist, Calabasas; Robert E. Guffin, La Habra; Walter M. Franklin, Sunland; James B. Crosby, Jr., North Hollywood; Glen N. Hallaway, Saugus; James G. Tellier, Canoga Park, all of Calif.

[73] Assignee: L.A. Gauge Co. Inc., Sun Valley, Calif.

[21] Appl. No.: 710,198

[22] Filed: Jul. 30, 1976

[51] Int. Cl.² ................................................ A61C 1/10
[52] U.S. Cl. ................................................ 32/27
[58] Field of Search ................................... 32/26, 27

[56] References Cited

U.S. PATENT DOCUMENTS 3,858,323  1/1975  Flatland ........................... 32/27

FOREIGN PATENT DOCUMENTS 1,161,157  3/1958  France ......................... 32/DIG. 7

Primary Examiner—Robert Peshock
Attorney, Agent, or Firm—Charles H. Schwartz

[57] ABSTRACT

An air-operated dental drill, including an elongated handle having a connector end for connection to a tubing connector and with an elongated air supply tube extending from the connector end to a head at the other end of the elongated handle and with the head supported on the other end of the handle and including an air turbine motor located within the head and with the outer housing of the head formed from a pair of complementary hollow members each mounted on opposite sides of a divider plate to accurately align and lock the pair of hollow members relative to each other and divide the air supplied to the air turbine motor. The air supply tube is threaded at both ends into complementary thread portions to lock the various members together. A removable light source is mounted at the head end of the dental drill and the drill includes a low voltage ring to supply power to the removable light source.

27 Claims, 13 Drawing Figures

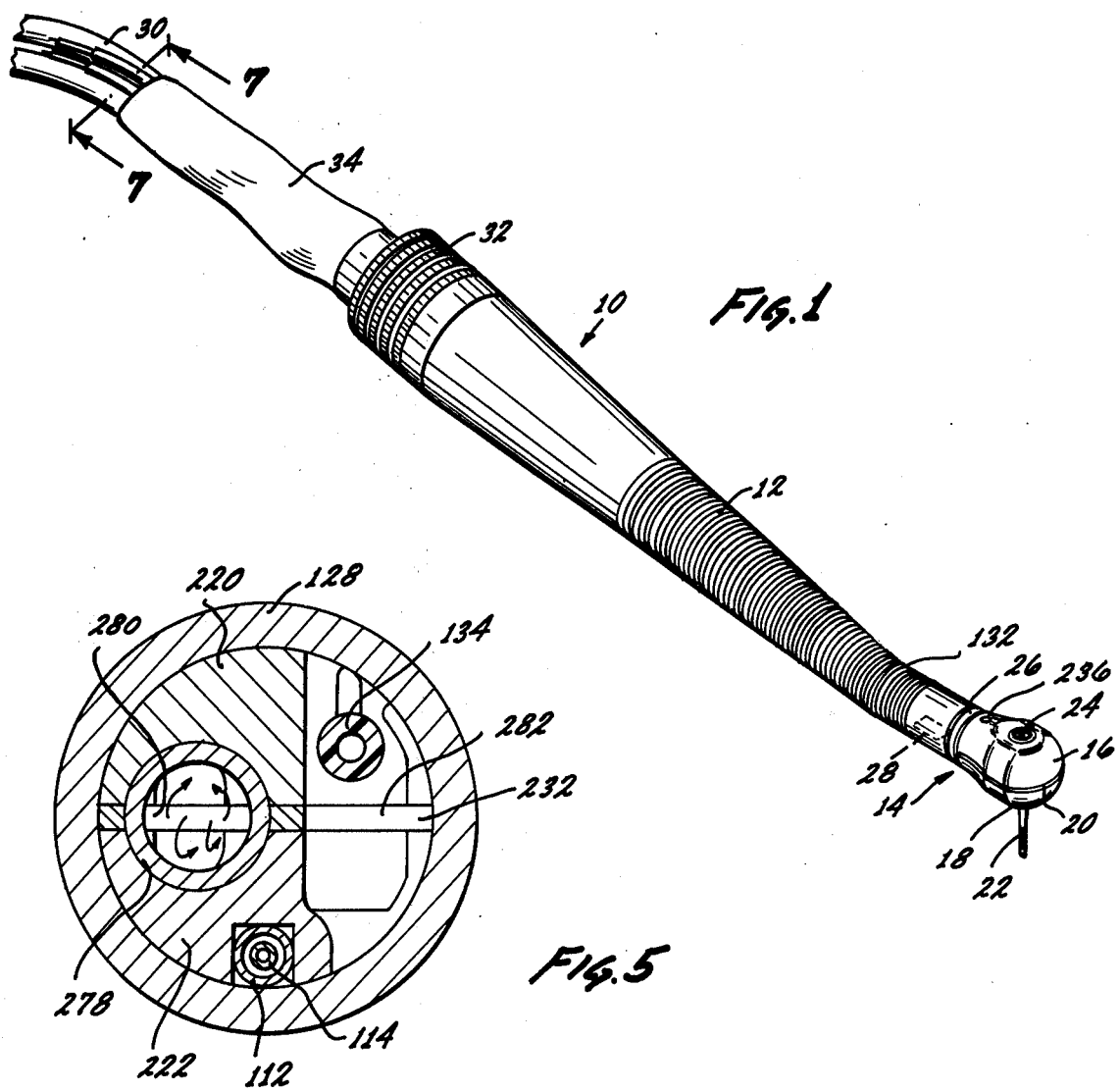

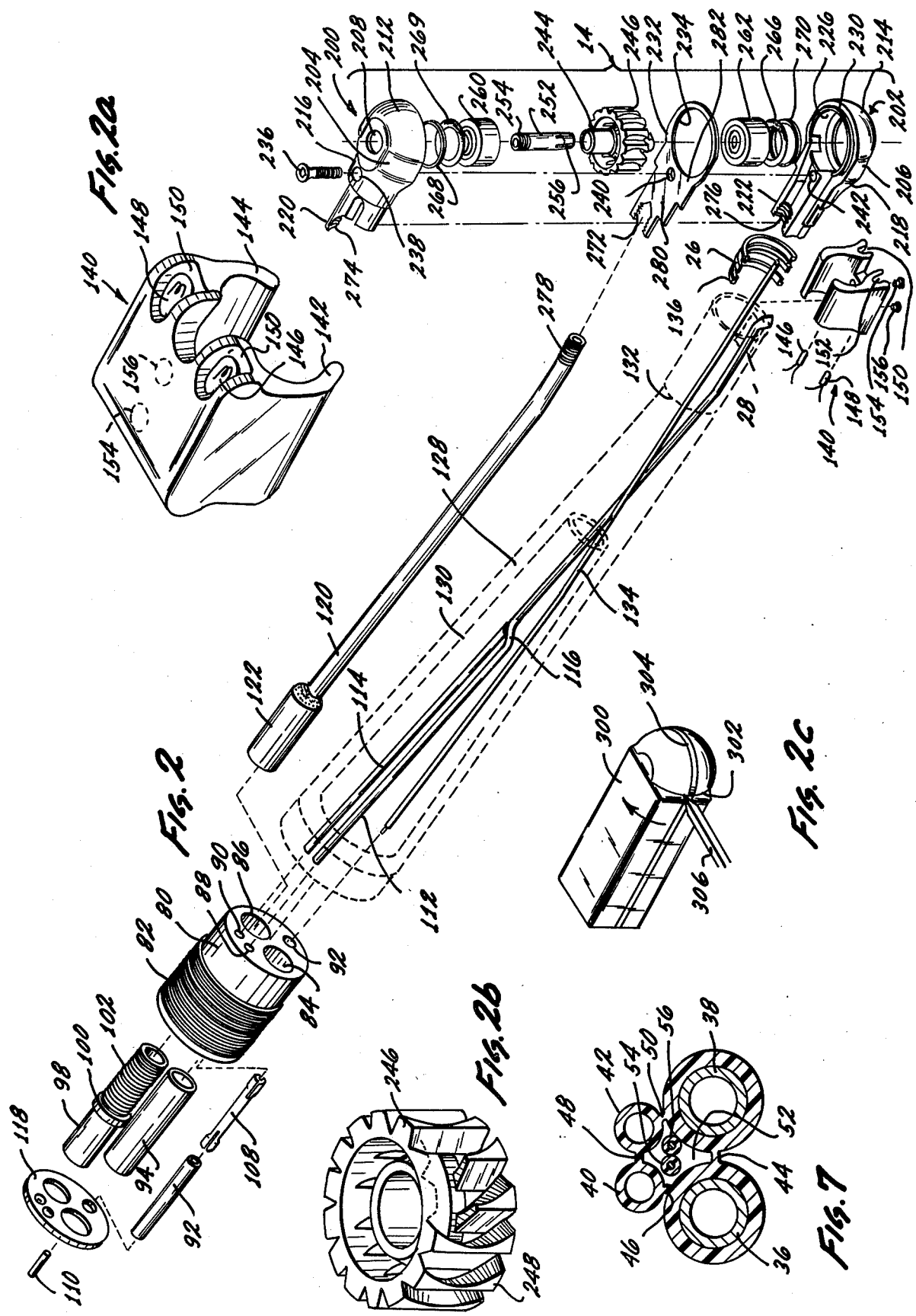

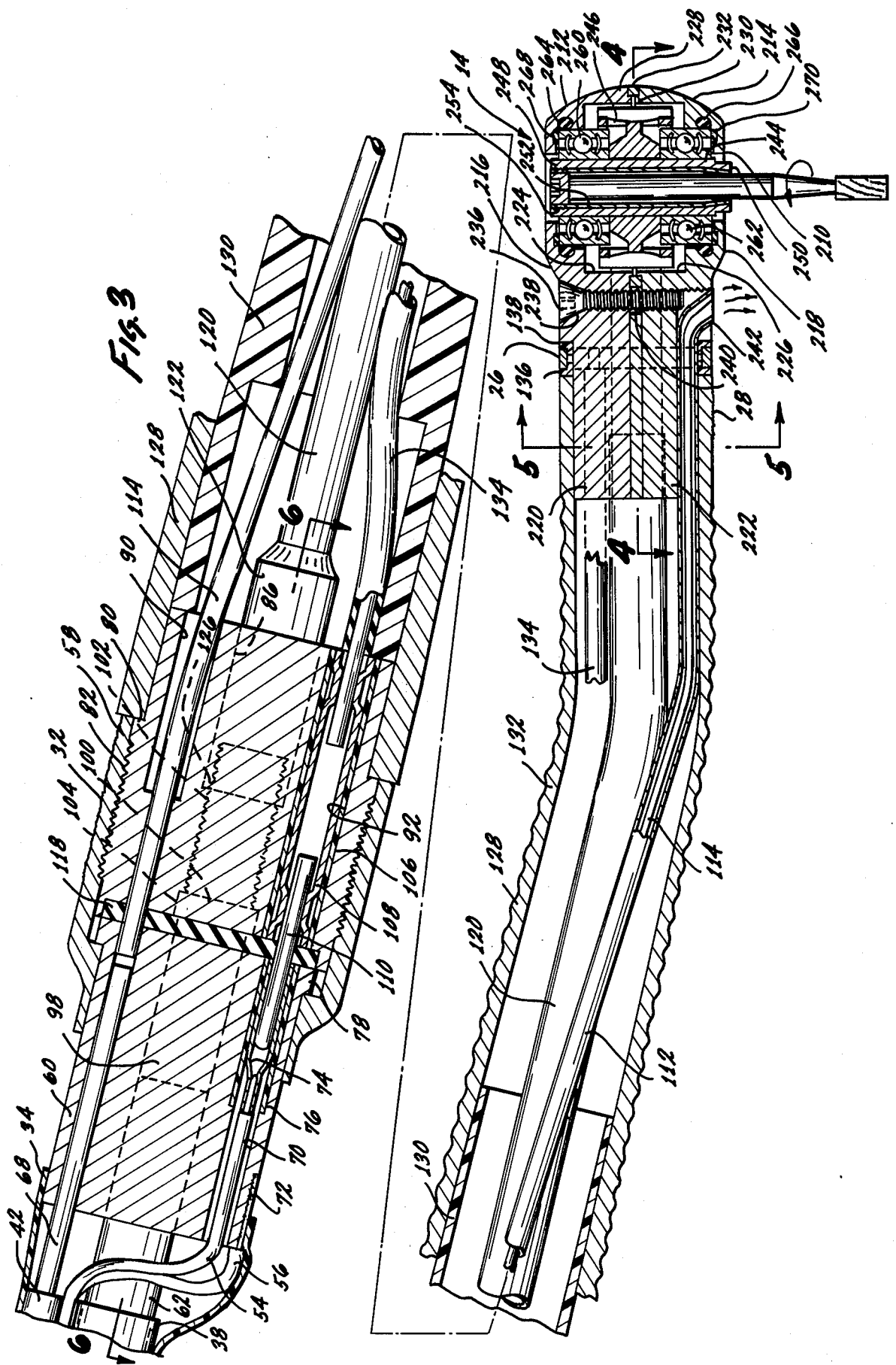

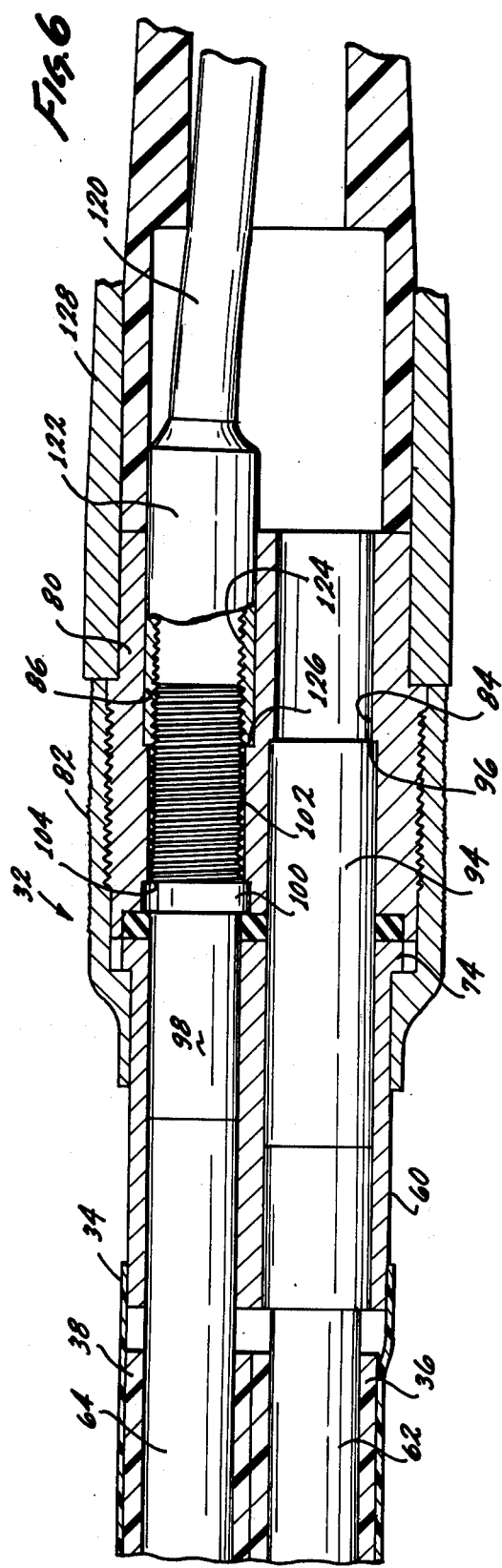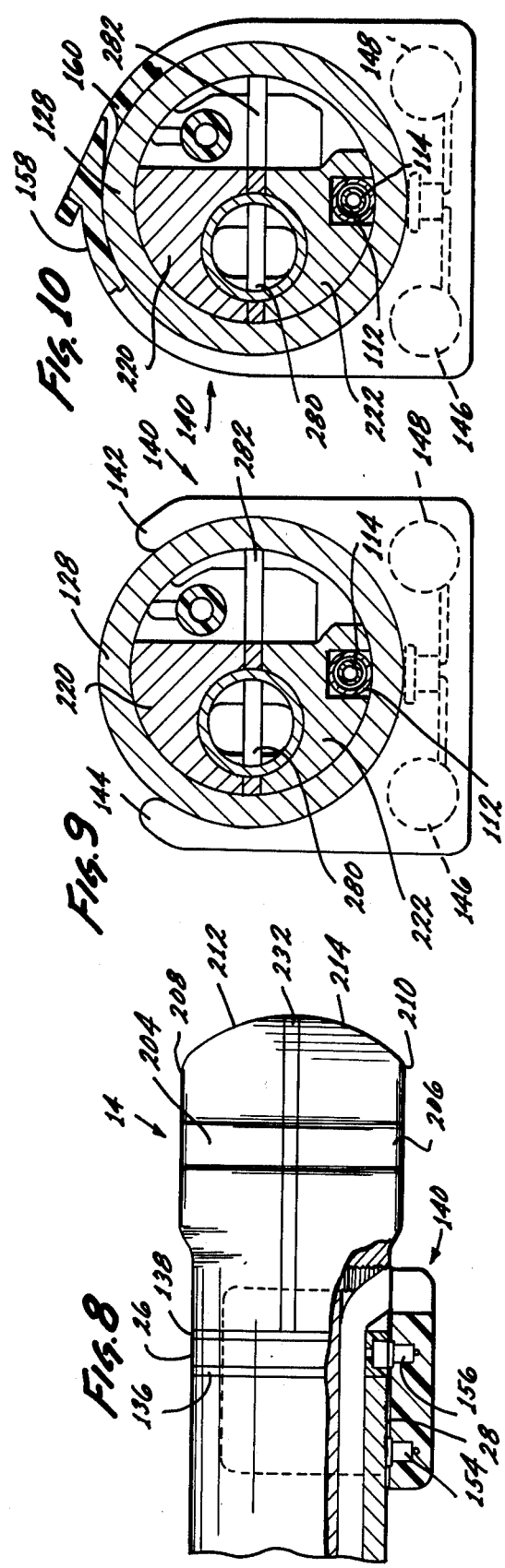

DENTAL DRILL

The present invention relates to an air-operated dental drill incorporating a split head with a divider plate. The divider plate serves a plurality of functions so as to provide for improved operation of the dental drill of the present invention. The dental drill of the present invention, although light in weight, has an improved performance by providing relatively high speed operation with an increase in torque and a smoothness of operation not achieved with prior art dental drills.

The dental drill of the present invention also includes a removable light source which may be used to provide for a source of light within the patient's mouth. The light source may also be easily removable when such light source is not desired for use by the dentist.

The dental drill of the present invention also includes an improved method of locking the various elements together so as to provide for rigidity in the structure of the dental drill. However, the method of locking also allows for the dental drill to be easily disassembled for any repair or reconstruction. The head portion of the drill is also machined with the divider plate acting as an alignment jig so as to provide for perfect alignment in the head of the dental drill which incorporates the air motor.

One type of dental drill commonly used by dentists for particular procedures is a high speed air-operated dental drill. These drills have advantages in that a very high speed may be obtained and with the air motor or turbine actually located within the head portion of the drill. Although these air-operated dental drills have found considerable acceptance in the dental field because of their high speed, safety and reliability, many of these drills are quite bulky and heavy and with the head portion quite large so as to limit their accessibility to parts of the patient's mouth. It is, therefore, desirable to reduce the size of the head portion as much as possible while at the same time maintaining the speed and the power of the drill.

The present invention provides for an air-operated dental drill which has a very small head portion but which provides for high speed operation and with a smooth power transmission to the drill under varying load conditions. The dental drill of the present invention actually provides for a greater torque output and a smoother operation than the prior art dental drills and provides for these advantages because of the unique structure of the design which structure is light in weight and small in size.

Specifically, the dental drill of the present invention includes a head portion which is formed as a split housing with a divider plate interconnecting the two portions of the split housing. The divider plate provides for a number of unique features in that it actually divides the air as it is passing to the rotor so as to give a better air flow over the blades of the rotor so as to achieve the high speed and smooth power output of the dental drill. The divider plate also operates as an alignment plate between the two portions of the split housing so as to lock the portions of the head together and to align all the parts within the head including the housing members, the rotor, and the various bearing members and seals. As the air leaves the rotor blades to be exhausted, the air is diffused by the divider plate so as to provide for a silencing of the exhaust air which in turn provides for quieter operation of the dental drill of the present invention.

The dental drill of the present invention also includes a rotor having blades which are shaped to increase the area of the blade in contact with the air so as to again provide for a smooth transition from the air flow to the rotation of the rotor which, in turn, provides for the rotation of the drill itself. The rotor blades are actually curved in two directions so as to maximize the effect of the air passing to and operating against the rotor blades.

In addition to the above structure for the head portion, the head portion may also include a ring member for supplying low voltage power to a removable source of the incandescent light. The light source may be constructed as a clip-on member to clip over the head portion and to contact the low voltage ring member. When the light source receives low voltage power, the light source provides for a relatively high amount of light within the patient's mouth. The light source itself is relatively small in structure so as not to interfere with the operation of the drill.

Most of the prior art air-operated dental drills have their various members force fitted together. This force fitting of the members makes it difficult to disassemble the drill for repair or renovation. The dental drill of the present invention uses an air intake tube threaded at both ends which tube threads into the head member at one end and a connector member at the other end so as to pull various elements together to form a rigid structure. However, it is relatively simple to disassemble the drill of the present invention since unthreading of the air tube provides for the disassembly of the various members.

During the manufacture of the air-operated dental drill of the present invention, the divider plate is also used as a fixture to hold the two portions of the split housing together. In this way, machining of the head, which includes the two portions of the split housing held together by the divider plate, provides for perfect aligning of the head structure using the same divider plate both as a machining fixture and also as a final part of the actual structure of the head.

A clearer understanding of the invention will be had with reference to the following description and drawings wherein FIG. 1 illustrates an overall perspective view of the external configuration of a dental drill of the present invention.

FIG. 2 is an exploded perspective view of the dental drill of the present invention.

FIG. 2(a) is an enlarged perspective view of the removable incandescent light source used as part of the dental drill of the present invention.

FIG. 2(b) is an expanded perspective view of the turbine rotor used with the dental drill of the present invention.

FIG. 2(c) is a view of the split head frame with the divider plate as partially machined to show the method of manufacture.

FIG. 3 is an expanded cross-sectional view of the dental drill of the present invention.

FIG. 4 is a cross-sectional view of the head portion taken along lines 4—4 of FIG. 3.

FIG. 5 is a cross-sectional view of the head portion taken along lines 5—5 of FIG. 3.

FIG. 6 is a cross-sectional view of the lower handle portion of the drill taken along lines 6—6 of FIG. 3.

FIG. 7 is a cross-sectional view of the tubes coupled to the drill taken along lines 7—7 of FIG. 1.

FIG. 8 is a side view, partially in cross-section, showing the light source at the head portion of the dental drill.

FIG. 9 illustrates one embodiment of a light source for use with the dental drill of the present invention; and FIG. 10 is a second embodiment of a light source for use with the dental drill of the present invention.

In FIG. 1, the external configuration of the dental drill of the present invention is shown as connected to an external tubing connector with the tubing attached. The dental drill includes a handle 10 having a knurled area 12 to provide a grip for the dentist. A head portion 14 is formed by a pair of split housing members 16 and 18 separated by a divider plate 20. A drill 22 is held by a chuck 24 for rotation within the head 14.

An insulated low voltage ring 26 provides low voltage power for a source of incandescent light and a grounding portion 28 is formed at the end of the handle 10. The exterior of the handle 10 including the knurled portion but excluding the grounding portion 28, may have an exterior finish such as a plating or an anodyzing. The grounding portion 28 is left exposed so as to provide for an electrical grounding connection for the incandescent light source.

A tubing assembly 30 is connected to a tubing connector 32 and with the tubing assembly 30 normally covered by a sheath of flexible material 34. As shown in FIG. 7, the tubing assembly consists of four tubing members 36, 38, 40, and 42, all joined together by web portions 44, 46, 48, and 50 so as to form an interior cavity 52.

The tube 38 normally provides for a supply of air and with the tube 36 providing for the air return path after the air is exhausted by the air motor. Tube 40 provides for a separate air supply and tube 42 provides for a supply of a coolant such as water and with the combination providing for an air-water mixture directed at the drilling site during the use of the air-operated drill of the present invention.

The present invention also contemplates the use of an incandescent light source and two fine electrical wires 54 and 56 are positioned in the cavity 52 defined between the plurality of tubing 36 through 42. One of the wires such as wire 56 is actually grounded to the tubing connector 32 and the other wire which carries low voltage, such as a 6 or 12 volts, extends through the drill and is connected to the low voltage ring 26 shown in FIG. 1.

FIGS. 3 and 6 illustrate the connection between the tubing and the tubing connector 32. The tubing connector 32 includes an interior threaded member 58 which is freely slideable along the outside surface of member 60. Member 60 forms the body of the tubing connector and includes a plurality of openings corresponding to the tubes 36 through 42 and with tube members 62 through 68 permanently received within the openings in the member 60. The flexible tubing 36 through 42 is fitted over the tube members 62 through 68. Tube member 66 is not shown but is substantially identical to tube member 68 and receives flexible tubing 40.

The body member 60 also includes an opening 70 to receive the low voltage wire 54. The ground wire 56 is attached, such as by soldering, to a recess portion 72 of the body member 60. The low voltage wire 54 is also coupled to a pin connector 74 which is insulated from the member 60 by insulated sleeve 76. In this way, the low voltage wire 54 may provide for low voltage power to the dental drill. The body member 60 also includes a flange portion 78 which serves as a stop for a complementary portion of the threaded member 58.

The connector end of the dental drill includes connector portions which are designed to be complementary to the tubing connector 32 so that all of the various tubings and electrical connections may be extended through the interior of the dental drill to the head. This may be seen with reference to the exploded view in FIG. 2 and also the cross-sectional views of FIGS. 3 and 6.

The connector end of the dental drill which connects with the cable connector 32 includes member 80 having an exterior threaded portion 82 which receives the interior threaded portion of the member 58. A plurality of openings 84 through 92 extends through the member 80 which openings correspond to the openings in the body member 60. Tubular member 94 is received in opening 84 and extends within opening 84 a specific distance as determined by stepped portion 96 in the opening 84. This may be seen in FIG. 6. A tubular member 98 having a stepped portion 100 and a threaded portion 102 is received within the opening 86. A stepped portion 104 in the opening 86 in combination with the stepped portion 100 of tubular member 98 provides for a stop for the tubular member 98 in the opening 96. The threaded portion 102 of the tubular member 98 cooperates with an interiorly threaded portion of the main air supply tube within the dental drill so as to lock the various members of the dental drill together in a manner to be described in a later portion of this specification.

The opening 92 receives an insulating sleeve 106 which sleeve 106 in turn receives an electrical connector tubular member 108. The electrical connector tubular member 108 is therefore maintained within the member 80 but insulated from the member 80 and the remaining portion of the dental drill. A removable pin member 110 may be used to interconnect the electrical connector member 108 in the connector end of the dental drill with the electrical connector member 74 in the cable connector 32. If the pin 110 is removed, the end of the dental drill is compatible with standard cable connectors which do not provide a low voltage source of power such as electrical wire 54. When the pin 110 is inserted the end of the dental drill is now compatible with the connector 32 which has been adapted to include a source of low voltage power.

The tubular members 94 and 98 extend from the end of the dental drill and mate with complementary openings in the cable connector 32 so as to provide for the supply of air and the air return paths from the tubular members 38 and 36.

The dental drill includes tubular members 112 and 114 which pass through the openings 88 and 90 in the member 80 and extend past the end of the dental drill to be received in complementary openings in the tubular connector 32. Therefore, the air and water which is supplied through the tubular members 40 and 42 are coupled to the tubular members 112 and 114 within the dental drill. The tubular member 112, which receives air, includes a bent portion 116 and the tubular member 114 is narrowed down at the bent portion 116 and passes within the member 112 so as to provide for the tubular members 112 and 114 to be in a concentric relationship. A mixture of air and water is supplied to the drilling site through the concentric tubing as shown in FIG. 3.

The connector end of the dental drill also includes a soft insulating member 118 which includes a plurality of openings to slip over the tubular members 94 and 98, the ends of the tubular members 112 and 114 and the pin member 110, so as to insulate the members from each other and provide a seal between the tubular connector 32 and the connector end of the dental drill.

An air supply tube 120 includes an enlarged end 122 which is received in the opening 86. The enlarged end 122 includes an interior threaded portion 124 which mates with the exterior threaded portion 102 of the tubular member 98. In addition, the opening 86 includes a stepped portion 126 to provide a stop for the end of the enlarged portion 102. The threading together of the two tubular members 98 and 120 provides for a locking at one end of the various components of the dental drill and with the stepped portions 104 and 126 controlling the desired distances to which the threaded portions 102 and 124 may be threaded together.

The dental drill includes an outer housing 128 which as shown in FIG. 1 has the knurled portion 12 to improve the grip of the drill during use. A tapered insulating member 130 is positioned within the drill housing and provides for sound insulation during the use of the drill. The outer housing 128 is also tapered and with the head portion offset at an angle of position 132 so as to provide for increased flexibility of the use of the drill in the patient's mouth.

In addition to the tubular members 120, 112, and 114, the outer housing 128 also contains an electrical wire 134 which interconnects with the electrical connector 108 and the low voltage ring 26. In this way, the low voltage electrical power is carried from the wire 54 through the tubular connector 32, through the connector end member 80 of the dental drill, and to the low voltage ring 26 so that the low voltage power is present at the head portion 14 of the dental drill. The low voltage ring 26 is insulated from the outer housing 128 and the head portion 14 by a pair of insulating rings 136 and 138.

The source of light is formed as a plastic member 140 which may, for example, include a pair of arm portions 142 and 144 which as shown in FIG. 9 wrap around the dental drill so as to securely maintain the light source in position. A pair of incandescent lights 146 and 148 are set in recessed areas 150 and 152 in the plastic member 140. A pair of contact members formed by rivets 154 and 156 provide contact between the light source and the low voltage ring 26 and the ground area 28. Each incandescent light 146 and 148 includes a pair of wires which wires are connected to the rivets 154 and 156. In this way, low voltage power passes through the low voltage ring 26 to the rivet 156 and to each one of the light sources 146 and 148 and back to the rivet 154 to the ground area 28. A complete electrical path is made and the incandescent lights are activated each time the removable light source is snapped on to the end of the dental drill and low voltage electrical power is supplied to the dental drill.

FIG. 10 illustrates an alternative method for attaching the incandescent light source to the dental drill and includes a pair of strap members 158 and 160 which interconnect by a clamping action to tightly hold the light source on the head end of the dental drill to ensure contact between the electrical contact areas 154 and 156 and the low voltage ring 26 and the ground area 28. Although low voltage is present at the end of the dental drill, it is of such a low potential, such as 6 or 12 volts, that it in no way creates an electrical hazard with the patient. Moreover, the incandescent light source may be rotated around the end of the dental drill so as to properly position the light source for the desired lighting within the patient's mouth during the use of the dental drill. The light source is very small and normally would not interfere with the use of the dental drill but if desired the light source can be removed and the dental drill used without the light source so as to even further minimize the size of the head area of the dental drill.

The head 14 of the dental drill of the present invention is composed of a split housing having an upper member 200 and a lower member 202. Each member includes a cylindrical portion 204 and 206 having flat ends 208 and 210 and rounded front portions 212 and 214. Each member 200 and 202 also includes rounded rear portions 216 and 218 which have a compound curve to extend from the cylindrical portions 204 and 206 to rear cylindrical portions 220 and 222.

The interior of the head member and specifically the portion which receives the air turbine motor is formed as stepped cylinders 224 and 226. Each stepped cylinder includes a rim portion 228 and 230 which extends outward so as to be received within a complementary opening within the divider plate 232. The divider plate 232 thereby accurately aligns the upper and lower members 200 and 202 together and locks them relative to each other. A screw member 236 passes through an opening 238 in upper member 200, an opening 240 in divider plate 232 and is received in a tapped opening 242 in lower member 202 so as to lock the upper and lower members together after they have been accurately aligned by the divider plate 232.

The stepped cylindrical interior formed by the members 200 and 202 and the divider plate 232 encloses the air turbine for rotation of the drill upon introduction of air to the motor through the air supply tube 120. The air turbine motor includes a shaft member 244 which supports a rotor 246 for rotation with the shaft. The rotor is shown in detail in FIG. 2(b) and can be seen to include curved blades 248 which are shaped in two directions. In other words, the blades 248 are curved inwardly and also scooped out so as to maximize the area which is in contact with the supply of air. This provides for the proper speed of rotation of the rotor and produces a smooth power under varying load conditions.

The shaft member 244 is hollow and has an interior threaded end 248 and a tapered end 250. A split chuck member 252 having a threaded end 254 and a split chuck end 256 is threaded into the shaft to receive a drill 258. As the chuck is threaded into the shaft 244, the split ends 256 are urged inwardly by the tapered section 250 of the shaft so as to lock the drill 258 in position.

The drill, shaft, chuck, and rotor are all supported for common rotation by a pair of ball bearings 260 and 262 which fit over the ends of the shaft 244. The bearings are held in position by O-rings 264 and 266 and a pair of resilient members 268 and 270 take up any end shake in the structure. It can be seen, therefore, that as air is introduced to the air motor, the rotor 246 on the shaft 244 is driven to rotate, thereby rotating the drill 258. This rotation occurs on a positive basis without any end shake and with a smooth transmission of power to the drill 258.

The end of the divider plate 232 includes a partially threaded portion 272 which cooperates with partial threaded portions 274 and 276 in the upper and lower members 200 and 202. The combination of the threaded portions 274 and 276 in the upper and lower members and the threaded portion 272 in the divider plate 232 forms a complete interior threaded member which cooperates with a threaded end 278 on the tube 120 so as to lock the head 14 at the end of the housing 128. It can be seen, therefore, that as the tube 120 threads into the head 14 at one end and threads into the member 98 at the other end, this pulls the member 80 and the head 14 towards each other to lock the entire dental drill together on the housing 128.

The tubular member 120 therefore provides the dual function of providing a supply of air to the rotor and also locks the members together to form a rigid structure for the dental drill. In addition, if it is necessary to disassemble the dental drill for repair or for restoration of the air turbine, the use of the member 120 provides for a simple way to unlock the various elements forming the dental drill.

The divider plate 232 not only serves as an alignment plate for the split members 200 and 202, it also provides for a divider plate for the supply of air to the rotor blades. As can be seen in FIG. 5, the end of the divider plate 232 and in particular the portion 280 subdivides the entrance to the air chamber for the supply of air to the rotor blades. This tends to split the air to give a more efficient air flow over the entire surface of the rotor blades so as to achieve the desired speed and provide for an increased torque and smoothness in the operation of the dental drill. As the air is returned from the rotor blades, it is again split by a portion 282 of the divider plate. This tends to diffuse the air so as to silence the return air to ensure quiet operation for the dental drill. The return of air is through the outer housing 128 to the return air opening 84 in the member 80.

The divider plate 232 therefore serves a multitude of functions. The plate provides for an alignment plate in aligning the split members of the head. The plate provides for a flow divider so as to divide the air to increase the efficiency of the transfer of the air to the rotor blades which, in turn, increases the torque and provides for smooth operation of the dental drill of the present invention. Another use of the divider plate 232 is during the manufacture of the head 14 as shoen in a partially machined state in FIG. 2(c).

In FIG. 2(c), a pair of flat members 300 and 302 have been machined to include the interior rims 228 and 230 shown in FIG. 3. The flat members 300 and 302 receive a plate member 304 which has already been machined with opening 234 as shown in FIG. 2. In this way, the partially formed divider plate 304 is used as an alignment tool during machining of the head 14. A tool 306 may be moved in accordance with a predetermined pattern against the members 300, 302, and 304 as they are rotating together so as to form the outside shape of the head member 14 which has the configuration of the members 200 and 202 locked together by the divider plate 232.

The interior portions of the members 200 and 202 may be milled out in a conventional fashion but the members 200 and 202 and the divider plate 232 will always be in perfect alignment since they were machined together using the divider plate as an alignment jig. This is important since the accuracy of the fit to the various members ensures that the dental drill will be able to sustain hard and continuous use by a dentist, with high speed, high torque, smoothness under varying loads and without vibration or chatter. The present invention provides for such a dental drill which is light weight, small in size, especially in the head area and incorporates the various improvements described above.

Although the invention has been described with reference to particular embodiments, it is to be appreciated various adaptations and modifications may be made and the invention is only to be limited by the appended claims.

We claim:

1. An air-operated dental drill, including
   an elongated handle including means at one end for connection to a tubing connector, and including an elongated tube extending from the means at one end to the other end of the elongated handle for providing a passage of air from one end of the handle to the other end of the handle,
   a head member supported at the other end of the handle and including an air turbine motor located within the head member for receiving the air passed to the other end of the handle, and
   the outer housing of the head member formed from a pair of complementary hollow members each mounted on opposite sides of a divider plate to accurately align and lock the pair of hollow members relative to each other.

2. The air-operated dental drill of claim 1 wherein one portion of the divider plate is located to intersect the end of the elongated tube at the other end of the handle and with the one portion dividing the air passed from the other end of the handle before the air is passed to the air turbine motor located within the head to provide a spread of the air flow to the turbine.

3. The air-operated dental drill of claim 2 wherein an additional portion of the divider plate is located adjacent the air turbine and with the additional portion dividing the air from the air turbine motor to diffuse the air to reduce the noise of the dental drill.

4. The air-operated dental drill of claim 1 wherein the elongated tube is threaded at both ends and with the means at one end of the elongated handle and the head member both including complementary threaded portions for locking together the head member, the elongated handle and the means at one end of the elongated handle with the threading together of the complementary threaded portions with the threaded ends of the elongated tube.

5. The air-operated dental drill of claim 1 additionally including an electrical wire extending from the one end to the other end of the handle and with the other end of the handle including an electrical contact area connected to the electrical wire and additionally including a light source supported in a housing and with the housing including a complementary contact area connected to the light source and with the housing removable supported on the other end of the handle with the contact areas engaging each other.

6. The air-operated dental drill of claim 5 wherein the contact area at the other end of the handle is formed as a ring.

7. The air-operated dental drill of claim 5 wherein the housing includes arm members to snap over and around the other end of the handle.

8. The air-operated dental drill of claim 5 wherein the housing includes clamp means to lock together around the other end of the handle.

9. The air-operated dental drill of claim 1 wherein the air turbine motor includes a rotor having a plurality of blades extending outward from the rotor to receive the air passed to the head member and with the shape of the blades curved ingward and scooped out to maximize the surface area in contact with the air.

10. The air-operated dental drill of claim 1 wherein the complementary hollow members and the divider plate form an interior stepped cylindrical chamber including cylindrical surfaces and with the air turbine including bearing members supporting a rotor and with the cylindrical surfaces receiving and supporting the bearing members and the rotor within the cylindrical chamber.

11. A head member for a dental drill, including
first and second hollow complementary housing members,
a divider plate,
means for mounting the first housing member on one side of the divider plate,
means for mounting the second housing member on the other side of the divider plate,
and with the divider plate accurately aligning the first and second hollow complementary housing members relative to each other to form an interior chamber.

12. The head member of claim 11 additionally includes an air turbine motor located within the interior chamber and a supply of air to the air turbine and with a portion of the divider plate located to intersect the supply of air for additionally diffusing the air supplied to the air turbine motor.

13. The head member of claim 11 wherein the first and second housing members each include a rim portion complementary to an opening in the divider plate and with the rim portions recessed in the opening on opposite sides to mount and align the housing members on the divider plate.

14. The head member of claim 13 wherein the first and second members are mounted on the divider plate during fabrication of the head member and with the formation of the head member including machining of the first and second members and the divider plate to a desired configuration and with the same divider plate also serving as alignment jig during the machining of the head to the desired configuration.

15. The head member of claim 13 wherein the first and second members and the divider plate each include complementary portions to form an elongated cylindrical portion extending away from the interior chamber and additionally including openings extending through the cylindrical portion to the interior chamber.

16. The head member of claim 15 additionally including an elongated handle having a cylindrical opening at one end for surrounding and receiving an end portion of the elongated cylindrical portion to mount the head member at the end of the handle.

17. The head member of claim 16 additionally including an elongated air supply tube positioned within the handle and connected to the elongated cylindrical portion to lock the head member at the end of the handle.

18. The head member of claim 15 additionally including a low voltage ring surrounding and insulated from the elongated portion.

19. The head member of claim 18 additionally including a source of light including a contact area and with the source of light including means for removable mounting the source of light on the head member with the contact area in contact with the low voltage ring.

20. The head member of claim 19 wherein the means for removable mounting includes a pair of arm members to snap over and around the low voltage ring.

21. The head member of claim 19 wherein the means for removable mounting includes a clamp means to lock the source of light on the head member.

22. The head member of claim 11 additionally including an air actuated rotor mounted for rotation within the interior chamber and with the rotor including a plurality of blades extending outward from the rotor and with the shape of the blades curved inward and scooped out to maximize the surface area.

23. The head member of claim 11 wherein the interior chamber is formed as a stepped cylinder and with the stepped cylinder chamber receiving an air turbine motor and with the divider plate diffusing air supplied to the motor and air coming from the motor.

24. A dental drill including
an elongated handle including means at one end for connection to a connector and including an elongated passage extending from the means at one end to the other end of the elongated handle,
a head member supported at the other end of the handle,
an electrical wire extending through the passage in the elongated handle from the one end to the other end of the handle,
the other end of the handle including a contact area connected to the electrical wire,
a light source supported in a housing and with the housing including a contact area connected to the light source and complementary to the contact area of the other end of the handle,
the housing removably supported on the other end of the handle for providing the engagement of the contact areas, and
the housing including arm members extending around at least a portion of the other end of the handle for supporting the housing in position.

25. The dental drill of claim 24 wherein the arm members snap over and around the other end of the handle.

26. The dental drill of claim 24 wherein the arm members include clamp means to lock together around the other end of the handle.

27. The dental drill of claim 24 wherein the contact area at the other end of the handle is formed as a ring.

* * * * *